(12) United States Patent
Randolph et al.

(10) Patent No.: US 6,709,638 B2
(45) Date of Patent: *Mar. 23, 2004

(54) ALKYLATION PROCESS

(75) Inventors: Bruce B. Randolph, Bartlesville, OK (US); Curtis B. Wood, Bartlesville, OK (US); Martyn E. Pfile, Bartlesville, OK (US)

(73) Assignee: ConocoPhillips Company, Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/371,766

(22) Filed: Feb. 21, 2003

(65) Prior Publication Data

US 2003/0130553 A1 Jul. 10, 2003

Related U.S. Application Data

(62) Division of application No. 09/702,582, filed on Oct. 31, 2000, now Pat. No. 6,552,241.

(51) Int. Cl.$^7$ .............................. B01J 8/02; C07C 2/60; C07C 2/58
(52) U.S. Cl. ....................... 422/188; 422/189; 422/190; 422/105
(58) Field of Search ................ 422/187–190, 422/105

(56) References Cited

U.S. PATENT DOCUMENTS

| | | | |
|---|---|---|---|
| 5,347,065 A | 9/1994 | Anderson | 585/724 |
| 5,386,076 A | 1/1995 | Child et al. | 585/802 |
| 5,759,937 A | 6/1998 | Hovis et al. | 502/36 |
| 5,767,335 A | 6/1998 | Anderson et al. | 585/723 |
| 6,096,553 A * | 8/2000 | Heald et al. | 436/40 |
| 6,228,650 B1 | 5/2001 | Moore et al. | 436/55 |

* cited by examiner

*Primary Examiner*—Hien Tran
(74) *Attorney, Agent, or Firm*—Jeffrey R. Anderson

(57) ABSTRACT

A system and/or process for removing water from an alkylation catalyst mixture of an alkylation process is disclosed. The process includes passing an alkylation reaction zone effluent to a settler for separation into a hydrocarbon phase and a catalyst mixture phase; passing at least a portion of the hydrocarbon phase, as a settler effluent stream containing alkylate, water, HF and volatility reducing additive, to a first separator; removing and condensing a first overhead stream from the first separator thereby forming an HF/water stream; passing the HF/water stream to a second separator for separation into a modified HF stream containing HF and volatility reducing additive and into an HF/water azeotrope stream containing HF and water; using the modified HF stream as a part of the alkylation catalyst mixture and; removing water from the system by removing the HF/water azeotrope stream from the second separator.

5 Claims, 4 Drawing Sheets

ALKYLATION PROCESS

This application is a division of application Ser. No. 09/702,582 filed Oct. 31, 2002, now U.S. Pat. No. 6,552, 241.

The present invention relates to a method and/or system for the alkylation of an olefin with an isoparaffin utilizing a catalyst mixture comprising a volatility reducing additive, hydrogen fluoride and water. More specifically, the invention relates to a method and/or system for removing water from the catalyst mixture to avoid water buildup therein.

BACKGROUND OF THE INVENTION

The use of catalytic alkylation processes to produce branched hydrocarbons having properties that are suitable for use as gasoline blending components is well known in the art. Generally, the alkylation of olefins by saturated hydrocarbons, such as isoparaffins, is accomplished by contacting the reactants with an acid catalyst to form a reaction mixture, settling the reaction mixture to separate the catalyst from the hydrocarbons, thereby forming a catalyst mixture phase and an alkylation reactor effluent, and further separating the alkylation reactor effluent, for example, by fractionation, to recover the separate product streams. Normally, the alkylation reactor effluent of the alkylation process contains hydrocarbons having five to ten carbon atoms per molecule. In order to have the highest quality gasoline blending stock, it is preferred for the alkylate hydrocarbons formed in the alkylation process to be highly branched and contain seven to nine carbon atoms per molecule.

Recent efforts to improve conventional hydrogen fluoride catalyzed alkylation processes have resulted in the development of new catalyst compositions that contain hydrogen fluoride and a volatility reducing additive. These new catalyst compositions have been found to be quite effective as an alkylation catalyst and to provide many other favorable benefits.

In such processes which include a volatility reducing additive in the catalyst, the regeneration of the catalyst mixture typically includes stripping a slip stream of the circulating catalyst mixture with an isoparaffin producing an overhead stream containing isoparaffin, hydrofluoric acid and water (preferably substantially absent of water) and a bottoms stream containing hydrofluoric acid (preferably in very small quantities), volatility reducing additive, and an acid soluble oil (ASO) produced as a by-product in the alkylation reaction. Because of the azeotrope formed between HF and water, it is often not possible to provide dry HF as the overhead stream. Thus, as described in U.S. Pat. No. 5,759,937 issued to Keith W. Hovis and Richard L. Anderson, a stripper side-draw stream is often required to remove water from the system by removing the HF/water azeotrope material from the sidedraw and allowing substantially water free HF to pass overhead. However, during certain upset conditions wherein excess water enters the system, either with the makeup HF or from feed contaminant upsets which can generate water, the sidedraw stream often cannot remove enough of the excess water. Excess water in the catalyst mixture can result in lower alkylation quality and can have other non-beneficial effects on the alkylation process, including corrosion problems. Therefore, development of an efficient process and/or system for removing water from a circulating alkylation catalyst mixture would be a significant contribution to the art.

BRIEF SUMMARY OF THE INVENTION

It is, thus, an object of the present invention to provide an improved process for removing water from an alkylation catalyst mixture.

A further object of the present invention is to provide an improved system to be used in removing water from an alkylation catalyst mixture which is economical in construction and reliable and efficient in operation.

A yet further object of the present invention is to provide a method and/or system for preventing the accumulation of water in the catalyst mixture of an alkylation process.

Still another object of the present invention is to provide a method and/or system for preventing the accumulation of water in the catalyst mixture of an alkylation process while minimizing the loss of HF with the water removed from the system.

A yet further object of the present invention is to provide an improved system to be used in preventing the accumulation of water in the catalyst mixture of an alkylation process which includes means for controlling the concentration of water in the catalyst mixture.

According to a first embodiment of the present invention, an alkylation process is provided and comprises the steps of:

a) contacting a hydrocarbon mixture comprising at least one olefin and at least one isoparaffin with a catalyst mixture comprising HF, a volatility reducing additive and water within a reaction zone to thereby produce a reaction zone effluent;

b) passing the reaction zone effluent to a settler wherein the reaction zone effluent is separated into a hydrocarbon phase and a catalyst mixture phase comprising HF, water and volatility reducing additive;

c) removing at least a portion of the hydrocarbon phase from the settler to form a settler effluent stream;

d) passing the settler effluent stream to a first separator;

e) removing an overhead stream from the first separator;

f) condensing at least a portion of the overhead stream to form an HF/water stream comprising HF, water and volatility reducing additive; and g) passing the HF/water stream to a second separator for separation into a modified HF stream comprising HF and volatility reducing additive and into an HF/water azeotrope stream comprising HF and water.

According to a second embodiment of the present invention, an alkylation process is provided and comprises the steps of:

a) contacting a hydrocarbon mixture comprising at least one olefin and at least one isoparaffin with a catalyst mixture comprising HF, a volatility reducing additive and water within a reaction zone to thereby produce a reaction zone effluent;

b) passing the reaction zone effluent to a settler wherein the reaction zone effluent is separated into a hydrocarbon phase and a catalyst mixture phase comprising HF, water, volatility reducing additive and acid soluble oil;

c) removing at least a portion of the hydrocarbon phase from the settler to form a settler effluent stream;

d) passing the settler effluent stream to a first separator;

e) removing a first separator overhead stream from the first separator;

f) condensing at least a portion of the first separator overhead stream to form an HF/water stream comprising HF, water and volatility reducing additive;

g) passing the HF/water stream to a second separator for separation into a modified HF stream comprising HF and volatility reducing additive and into an HF/water azeotrope stream comprising HF and water; and h) passing at least a portion of the catalyst mixture phase to a third separator for separation into a third separator overhead stream comprising HF and water and into a third separator bottoms stream comprising HF, water, ASO and volatility reducing additive.

According to a third embodiment of the present invention, an alkylation process is provided and comprises the steps of:

a) contacting a hydrocarbon mixture comprising at least one olefin and at least one isoparaffin with a catalyst mixture comprising HF, a volatility reducing additive and water within a reaction zone to thereby produce a reaction zone effluent;

b) passing the reaction zone effluent to a settler wherein the reaction zone effluent is separated into a hydrocarbon phase and a catalyst mixture phase comprising HF, water, volatility reducing additive and acid soluble oil;

c) removing at least a portion of the hydrocarbon phase from the settler to form a settler effluent stream;

d) passing the settler effluent stream to a first separator;

e) passing at least a portion of the catalyst mixture phase to a second separator for separation into a second separator overhead stream comprising HF and water and separation into a second separator bottoms stream comprising HF, water, ASO and volatility reducing additive;

f) blocking the passing of the at least a portion of the catalyst mixture phase to the second separator in step e;

g) removing a first separator overhead stream from the first separator;

h) condensing at least a portion of the first separator overhead stream to form an HF/water stream comprising HF, water and volatility reducing additive; and i) passing the HF/water stream to the second separator for separation into a modified HF stream comprising HF and volatility reducing additive and into an HF/water azeotrope stream comprising HF and water.

According to a fourth embodiment of the present invention, an alkylation system is provided and comprises:

an alkylation reactor;

a settler, having an upper portion, an intermediate portion and a lower portion;

a first separator, having an upper portion, an intermediate portion and a lower portion;

a second separator, having an upper portion, an intermediate portion and a lower portion;

a third separator, having an upper portion, an intermediate portion and a lower portion;

a condenser unit;

first conduit means operably related to the alkylation reactor for introducing a hydrocarbon feedstock comprising olefins and isoparaffins into the alkylation reactor;

second conduit means operably related to the alkylation reactor for introducing a catalyst mixture comprising a volatility reducing additive, hydrofluoric acid and water into the alkylation reactor;

third conduit means operably related to the alkylation reactor and operably related to the settler for withdrawing a reaction zone effluent from the alkylation reactor and for introducing the reaction zone effluent into the intermediate portion of the settler, the upper portion of the settler being operable for containing a hydrocarbon phase separated from the reaction zone effluent and the lower portion of the settler being operable for containing a catalyst mixture phase separated from the reaction zone effluent;

fourth conduit means operably related to the settler and operably related to the first separator for withdrawing at least a portion of the hydrocarbon phase from the upper portion of the settler and for introducing the at least a portion of the hydrocarbon phase into the intermediate portion of the first separator;

fifth conduit means operably related to the first separator and operably related to the condenser unit for withdrawing an overhead stream from the upper portion of the first separator and for introducing the overhead stream into the condenser unit;

sixth conduit means operably related to the condenser unit and operably related to the second separator for withdrawing an HF/water stream from the condenser unit and for introducing the HF/water stream into the intermediate portion of the second separator;

seventh conduit means operably related to the sixth conduit means and operably related to the settler for withdrawing a portion of the HF/water stream from the sixth conduit means and for introducing the portion of the HF/water stream into the intermediate portion of the settler;

eighth conduit means operably related to the first separator for withdrawing an alkylate product stream from the first separator;

ninth conduit means operably related to the settler and operably related to the alkylation reactor for withdrawing at least a portion of the catalyst mixture phase from the settler and for introducing the at least a portion of the catalyst mixture phase into the alkylation reactor;

tenth conduit means operably related to the settler and operably related to the second separator for withdrawing a catalyst mixture phase regeneration stream from the lower portion of the settler and for introducing the catalyst mixture phase regeneration stream into the intermediate portion of the second separator;

eleventh conduit means operably related to the second separator and operably related to the settler for withdrawing a second separator overhead stream from the upper portion of the second separator and for introducing the second separator overhead stream to the intermediate portion of the settler;

twelfth conduit means operably related to the second separator and operably related to the third separator for withdrawing a second separator bottoms stream from the lower portion of the second separator and for introducing the second separator bottoms stream to the intermediate portion of the third separator, the upper portion of the third separator being operable for containing ASO and the lower portion of the third separator being operable for containing HF and volatility reducing additive;

thirteenth conduit means operably related to the twelfth conduit means for withdrawing a purge stream from the twelfth conduit means; and fourteenth conduit means operably related to the third separator and operably related to the settler for withdrawing a third separator bottoms stream from the lower portion of the third separator and for introducing at least a portion of the third separator bottoms stream into the intermediate portion of the settler.

The alkylation system can further comprise control means operably related to the sixth conduit means, the seventh conduit means, the ninth conduit means, the tenth conduit means, the twelfth conduit means, and the thirteenth conduit means for controlling the water concentration in the catalyst mixture phase regeneration stream to a level equal to a set point water wt. %, based on the total weight of the catalyst mixture phase.

Other objects and advantages will become apparent from the detailed description and the appended claims.

DETAILED DESCRIPTION OF THE INVENTION

The hydrocarbon mixture suitable for use in the present invention as the alkylation reaction zone feed comprises at least one olefin and at least one isoparaffin. The olefin preferably contains from 3 to 5 carbon atoms per molecule and the isoparaffin preferably contains from 3 to 6 carbon atoms per molecule.

The catalyst mixture suitable for use in the present invention comprises a volatility reducing additive, a hydrogen halide, preferably hydrogen fluoride, and water. The catalyst mixture can also comprise acid soluble oil, which is a by-product of the alkylation process. The volatility reducing additive can be any compound effective in reducing the volatility of a mixture resulting from the addition of the volatility reducing additive to hydrofluoric acid. More particularly, the volatility reducing additive can be a compound selected from the group consisting of sulfone, ammonia, methylamines, ethylamines, propylamines, butylamines, pentylamines, pyridine, alkylpyridines, picoline, melamine, hexamethylene-tetramine and the like.

The sulfones suitable for use in this invention are the sulfones of the general formula

wherein R and $R^1$ are monovalent hydrocarbon alkyl or aryl substituents, each containing from 1 to 8 carbon atoms, and wherein R and $R^1$ can be the same or different. Examples of suitable sulfones include, but are not limited to, dimethylsulfone, di-n-propylsulfone, diphenylsulfone, ethylmethylsulfone and alicyclic sulfones wherein the $SO_2$ group is bonded to a hydrocarbon ring. In such a case, R and $R^1$ are forming together a branched or unbranched hydrocarbon divalent moiety preferably containing from 3 to 12 carbon atoms. Among the latter, tetramethylenesulfone or sulfolane, 3-methylsulfolane and 2,4-dimethylsulfolane are more particularly suitable since they offer the advantage of being liquid at process operating conditions of concern herein. These sulfones may also have substituents, particularly one or more halogen atoms, such as for example, chloromethylethylsulfone. These sulfones may advantageously be used in the form of mixtures of any two or more thereof. The most preferred volatility reducing additive is sulfolane.

Figure 1:
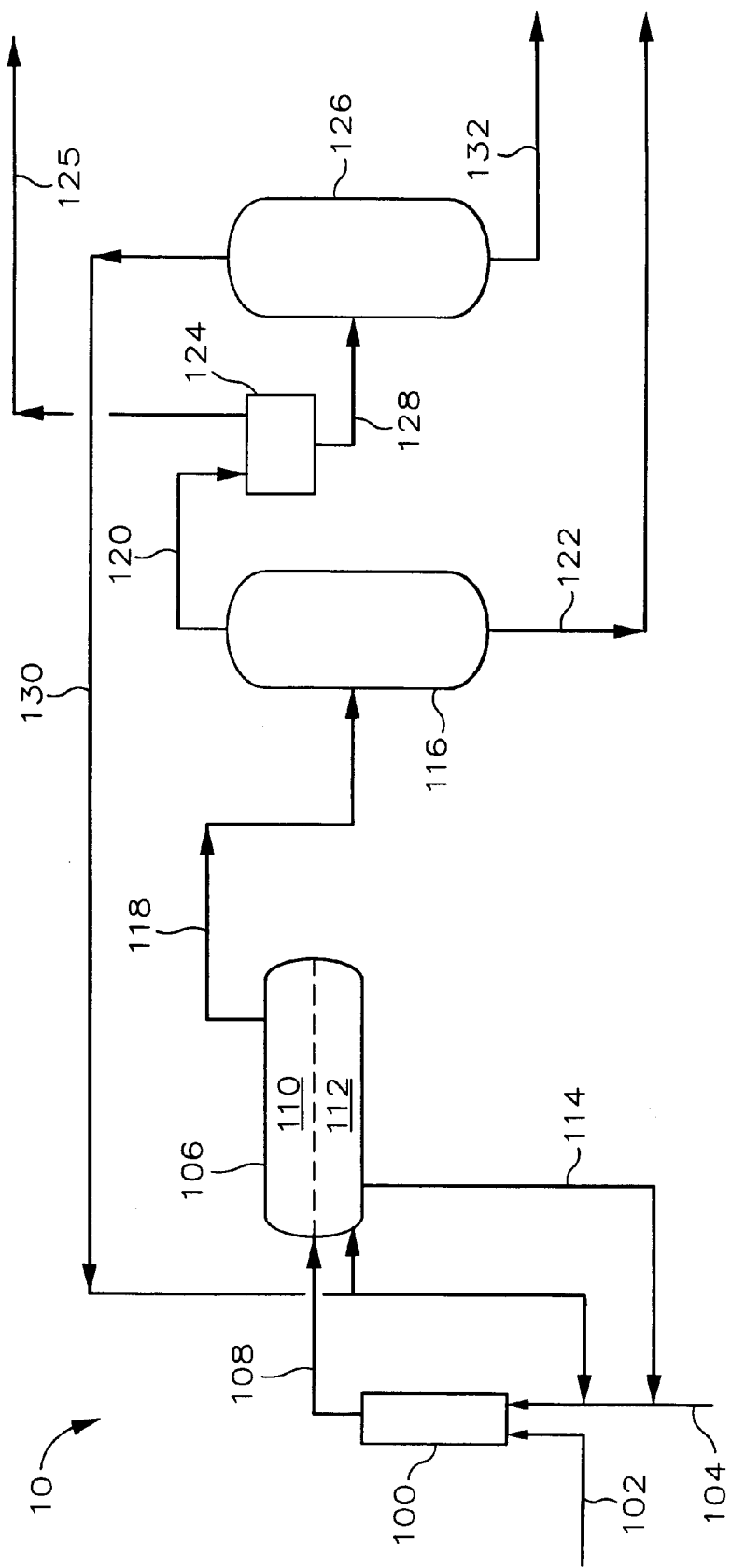
FIG. 1 is a schematic flow diagram presenting an embodiment of the present invention.

According to a first embodiment of the present invention, and referring to FIG. 1, an alkylation process system 10 is depicted which can comprise, consist of, or consist essentially of the following steps.

The hydrocarbon mixture and the catalyst mixture are passed to a reactor 100, defining a reaction zone, via conduits 102 and 104, respectively. A reaction zone effluent is passed from reactor 100 to a settler 106 via conduit 108 wherein the reaction zone effluent is separated into a hydrocarbon phase 110 comprising, consisting of, or consisting essentially of unreacted isoparaffins, alkylate product, HF, water and volatility reducing additive, and a catalyst mixture phase 112 comprising, consisting of, or consisting essentially of HF, water and volatility reducing additive.

The combined total wt. % of HF, water and volatility reducing additive contained in the hydrocarbon phase 110 is typically in the range of from about 0.1 to about 2, more typically from about 0.4 to about 1.5, and most typically from 0.5 to 1.2.

At least a portion of the catalyst mixture phase 112 can be recycled to reactor 100 via conduit 114 for use as at least a portion of said catalyst mixture.

At least a portion of the hydrocarbon phase 110 can be removed from settler 106 to form a settler effluent stream. The settler effluent stream is then passed to a first separator 116 via conduit 118 from which an overhead stream and a bottoms stream are removed via conduits 120 and 122, respectively. The overhead stream generally comprises, consists of, or consists essentially of unreacted isoparaffins and/or olefins, HF, volatility reducing additive and water. The bottoms stream comprises, consists of, or consists essentially of alkylate product and volatility reducing additive.

At least a portion of the overhead stream is passed to a condenser 124 via conduit 120 wherein at least a portion of the overhead stream is condensed to form an HF/water stream comprising, consisting of, or consisting essentially of HF, water and volatility reducing additive. Light gases, such as unreacted isoparaffin and/or olefin can be removed from condenser 124 via conduit 125. The HF/water stream can be passed to a second separator 126 via conduit 128 for separation into a modified HF stream comprising, consisting of, or consisting essentially of HF and volatility reducing additive and into an HF/water azeotrope stream comprising, consisting of, or consisting essentially of HF, volatility reducing additive and water. At least a portion of the modified HF stream can be passed to reactor 100 via conduits 130 and 104 for use as at least a portion of the catalyst mixture. The HF/water azeotrope stream can be passed via conduit 132 to a treatment unit for neutralization of the HF.

Figure 2:
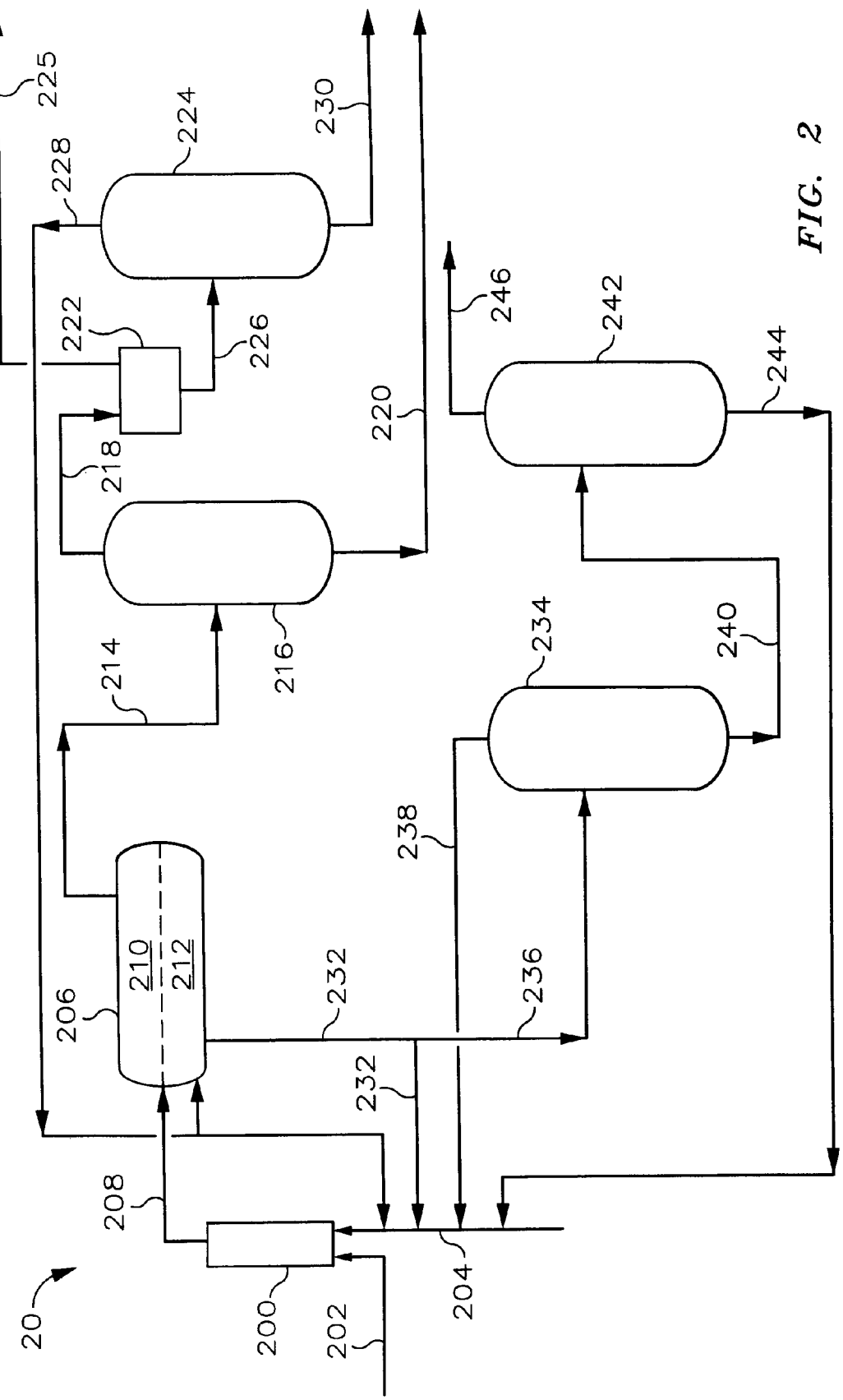
FIG. 2 is a schematic flow diagram presenting an embodiment of the present invention.

According to a second embodiment of the present invention, and referring to FIG. 2, an alkylation process system 20 is depicted which can comprise, consist of, or consist essentially of the following steps.

The hydrocarbon mixture and the catalyst mixture are passed to a reactor 200, defining a reaction zone, via conduits 202 and 204, respectively. A reaction zone effluent is passed to a settler 206 via conduit 208 wherein the reaction zone effluent is separated into a hydrocarbon phase 210 comprising, consisting of, or consisting essentially of unreacted isoparaffins, alkylate product, HF, water and volatility reducing additive and a catalyst mixture phase 212 comprising, consisting of, or consisting essentially of HF, water, volatility reducing additive and acid soluble oil.

The combined total wt. % of HF, water and volatility reducing additive contained in the hydrocarbon phase is typically in the range of from about 0.1 to about 2, more typically from about 0.4 to about 1.5, and most typically from 0.5 to 1.2.

At least a portion of the hydrocarbon phase 210 can be removed from settler 206 via conduit 214 to form a settler effluent stream comprising, consisting of, or consisting essentially of unreacted isoparaffin, alkylate product, HF, water and volatility reducing additive. The settler effluent stream can be passed to a first separator 216 via conduit 214 from which a first separator overhead stream and an alkylate product stream are removed via conduits 218 and 220, respectively. The first separator overhead stream generally comprises, consists of, or consists essentially of unreacted isoparaffins and/or olefins, HF, volatility reducing additive and water. The alkylate product stream comprises, consists of, or consists essentially of alkylate product and volatility reducing additive. At least a portion of the first separator overhead stream can be passed to a condenser 222 via conduit 218 wherein at least a portion of the overhead stream is condensed to form an HF/water stream comprising, consisting of, or consisting essentially of HF, water and volatility reducing additive. Light gases, such as unreacted isoparaffin and/or olefin can be removed from condenser 222 via conduit 225.

The HF/water stream can be passed to a second separator 224 via conduit 226 for separation into a modified HF stream comprising, consisting of, or consisting essentially of HF and volatility reducing additive and for separation into an HF/water azeotrope stream comprising, consisting of, or consisting essentially of HF and water. At least a portion of the modified HF stream can be used as at least a portion of the catalyst mixture. For example, at least a portion of the modified HF stream can be passed to reactor 200 via conduits 228 and 204 for use as at least a portion of the catalyst mixture. The HF/water azeotrope stream can be removed from second separator 224 via conduit 230 and passed to a treatment unit for neutralization of HF.

At least a portion of the catalyst mixture phase 212 can be recycled to reactor 200 via conduits 232 and 204 for use as at least a portion of the catalyst mixture. In addition, at least a portion of the catalyst mixture phase can be passed to a third separator 234 via conduits 232 and 236 for separation into a third separator overhead stream comprising, consisting of, or consisting essentially of HF and water and into a third separator bottoms stream comprising, consisting of, or consisting essentially of HF, water, ASO and volatility reducing additive. At least a portion of the third separator overhead stream can be used at least a portion of the catalyst mixture. For example, at least a portion of the third separator overhead stream can be passed from third separator 234 to reactor 200 via conduits 238 and 204 for use as at least a portion of the catalyst mixture. The third separator bottoms stream can be passed via conduit 240 to a fourth separator 242 for separation into an ASO stream comprising, consisting of, or consisting essentially of ASO and into a volatility reducing additive stream comprising, consisting of, or consisting essentially of HF, water and volatility reducing additive. At least a portion of the volatility reducing additive stream can be used as at least a portion of the catalyst mixture. For example, at least a portion of the volatility reducing additive stream can be passed from fourth separator 242 to reactor 200 via conduits 244 and 204 for use as at least a portion of the catalyst mixture. At least a portion of the ASO stream can be removed from fourth separator 242 via conduit 246.

Figure 3:
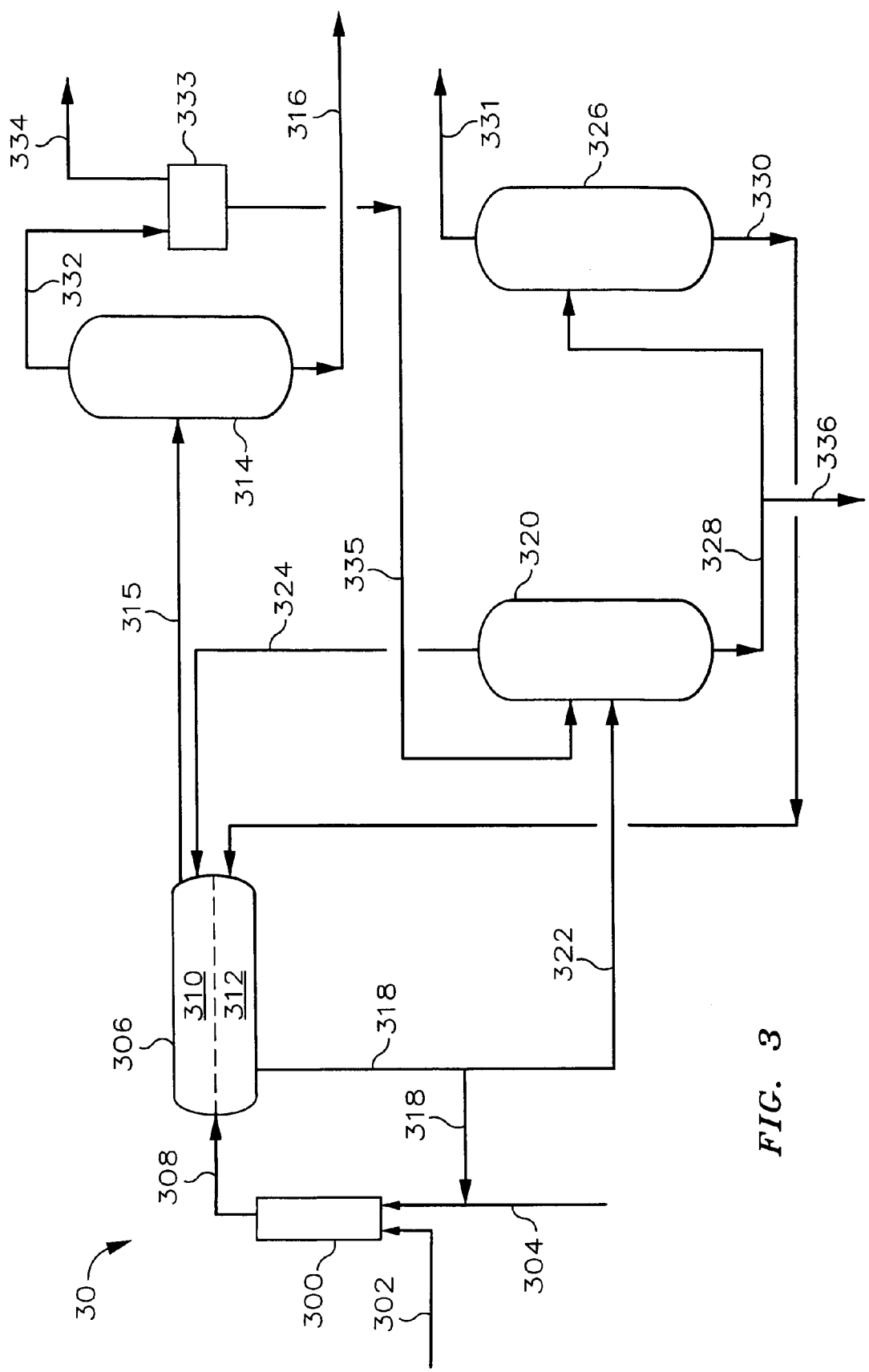
FIG. 3 is a schematic flow diagram presenting an embodiment of the present invention.

According to a third embodiment of the present invention, and referring to FIG. 3, an alkylation process system 30 is depicted which can comprise, consist of, or consist essentially of the following steps.

The hydrocarbon mixture and the catalyst mixture are passed to a reactor 300, defining a reaction zone, via conduits 302 and 304, respectively. A reaction zone effluent is passed to a settler 306 via conduit 308 wherein the reaction zone effluent is separated into a hydrocarbon phase 310 comprising, consisting of, or consisting essentially of unreacted isoparaffin, alkylate product, HF, water and volatility reducing additive, and into a catalyst mixture phase 312 comprising, consisting of, or consisting essentially of HF, water, volatility reducing additive and acid soluble oil. At least a portion of the hydrocarbon phase can be removed from the settler to form a settler effluent stream. The settler effluent stream can be passed to a first separator 314 via conduit 315 from which an alkylate product stream can be removed from the bottom of first separator 314 via conduit 316.

At least a portion of the catalyst mixture phase 312 can be recycled to reactor 300 via conduits 318 and 304 for use as the catalyst mixture. In addition, at least a portion of the catalyst mixture phase 312 can be passed to a second separator 320 via conduits 318 and 322 for separation into a second separator overhead stream comprising, consisting of, or consisting essentially of HF, volatility reducing additive and water and separation into a second separator bottoms stream comprising, consisting of, or consisting essentially of HF, water, ASO and volatility reducing additive. At least a portion of the second separator overhead stream can be used as at least a portion of the catalyst mixture. For example, at least a portion of the second separator overhead stream can be passed from second separator 320 to settler 306 via conduit 324. The second separator bottoms stream can be passed to a third separator 326 via conduit 328 for separation into an ASO stream comprising, consisting of, or consisting essentially of ASO and into a volatility reducing additive stream comprising, consisting of, or consisting essentially of HF, water, and volatility reducing additive. At least a portion of the volatility reducing additive stream can be used as at least a portion of the catalyst mixture. For example, at least a portion of the volatility reducing additive stream can be passed to settler 306 to become a part of catalyst mixture phase 312 via conduit 330. The ASO stream can be removed from third separator 326 via conduit 331.

At any time it is deemed necessary, and more specifically when the concentration of water in the catalyst mixture phase exceeds 3 wt. %, based on the total weight of the catalyst mixture phase, the passing of the at least a portion of the catalyst mixture phase 312 to second separator 320 via conduits 322 and 318 and the passing of the second separator bottoms stream to third separator 326 via conduit 328 can each be blocked. A first separator overhead stream can be removed from first separator 314 via conduit 332. At least a portion of the first separator overhead stream can be passed to a condenser 333 via conduit 332 wherein at least a portion of the overhead stream is condensed to form an HF/water stream comprising, consisting of, or consisting essentially of HF, water and volatility reducing additive. Light gases, such as unreacted isoparaffin and/or olefin can be removed from condenser 333 via conduit 334. The HF/water stream can be passed to second separator 320 via conduit 335 for separation into a modified HF stream comprising, consisting of, or consisting essentially of HF and volatility reducing additive and into an HF/water azeotrope stream comprising, consisting of, or consisting essentially of HF and water. At least a portion of the modified HF stream can be used as at least a portion of the catalyst mixture. More particularly, at least a portion of the modified HF stream can be passed to settler 306 from second separator 320 via conduit 324. The HF/water azeotrope stream can be removed from second separator 320 via conduits 328 and 336 and can be passed to a treatment unit for neutralization of HF.

Figure 4:
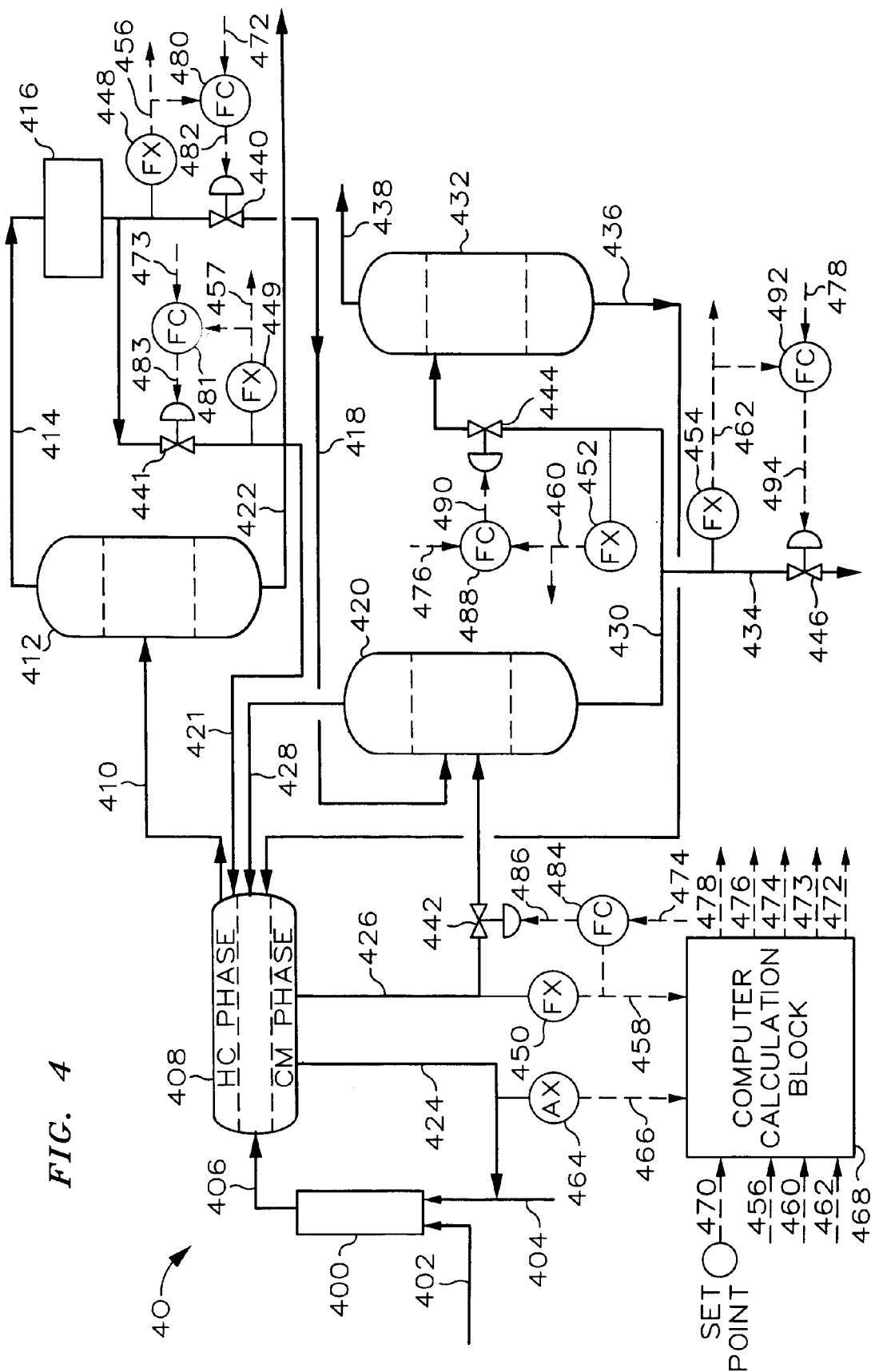
FIG. 4 is a schematic flow diagram presenting an embodiment of the present invention including a control system.

According to a fourth embodiment of the present invention, and referring to FIG. 4, therein is illustrated the inventive system or apparatus 40 including an alkylation reactor 400 defining an alkylation reaction zone. The alkylation reactor 400 is operably related by connection in fluid flow communication to a conduit 402 providing first conduit means for introducing a hydrocarbon feedstock comprising, consisting of, or consisting essentially of olefins and isoparaffins into said alkylation reactor. The alkylation reactor 400 is also operably related by connection in fluid flow communication to a conduit 404 providing second conduit means for introducing a catalyst mixture comprising, consisting of, or consisting essentially of a volatility reducing additive, hydrofluoric acid and water into the alkylation reactor 400. The alkylation reactor 400 provides means for alkylating at least a portion of the hydrocarbon feedstock to thereby produce a reaction zone effluent.

The alkylation reactor 400 is operably related by connection in fluid flow communication to a conduit 406 providing third conduit means for withdrawing the reaction zone effluent from the alkylation reactor 400 and for introducing the reaction zone effluent into the intermediate portion of a settler 408 having an upper portion, intermediate portion and lower portion. The upper portion of settler 408 is operable for containing a hydrocarbon phase separated from the reaction zone effluent and the lower portion of settler 408 is operable for containing a catalyst mixture phase separated from the reaction zone effluent. Settler 408 is operably related in fluid flow communication with a conduit 410 providing fourth conduit means for withdrawing at least a portion of the hydrocarbon phase from the upper portion of settler 408 and for introducing at least a portion of the hydrocarbon phase into the intermediate portion of a first separator 412 having an upper portion, intermediate portion and lower portion. First separator 412 is operably related by connection in fluid flow communication via conduit 414 with a condenser unit 416. Conduit 414 provides fifth conduit means for withdrawing an overhead stream from the upper portion of first separator 412 and introducing the overhead stream into condenser unit 416. Condenser unit 416 is operably related by connection in fluid flow communication via conduit 418 with a second separator 420 having an upper portion, intermediate portion and lower portion. Conduit 418 provides sixth conduit means for withdrawing an HF/water stream from condenser unit 416 and for introducing the HF/water stream into the intermediate portion of second separator 420.

Conduit 421 is operably related by connection in fluid flow communication with conduit 418 and settler 408 and provides seventh conduit means for withdrawing a portion of the HF/water stream from conduit 418 and for introducing the portion of the HF/water stream into the intermediate portion of settler 408.

First separator 412 is operably related in fluid flow communication to a conduit 422 providing eighth conduit means for withdrawing an alkylate product stream from first separator 412. Settler 408 is operably related in fluid flow communication via conduit 404 and via conduit 424, providing ninth conduit means, with alkylation reactor 400 for withdrawing at least a portion of the catalyst mixture phase from settler 408 and for introducing the at least a portion of the catalyst mixture phase into alkylation reactor 400. In addition, settler 408 is operably related via conduit 426, providing tenth conduit means, to second separator 420 for withdrawing a catalyst mixture phase regeneration stream from the lower portion of settler 408 and for introducing the catalyst mixture phase regeneration stream into the intermediate portion of second separator 420.

Second separator 420 is operably related in fluid flow communication via conduit 428 to settler 408. Conduit 428 provides eleventh conduit means for withdrawing a second separator overhead stream from the upper portion of second separator 420 and for introducing the second separator overhead stream to the intermediate portion of settler 408. Second separator 420 is operably related in fluid flow communication via conduit 430 to a third separator 432 having an upper portion, intermediate portion and a lower portion. Conduit 430 provides twelfth conduit means for withdrawing a second separator bottoms stream from the lower portion of second separator 420 and for introducing the second separator bottoms stream to the intermediate portion of third separator 432. The upper portion of third separator 432 is operable for containing ASO and the lower portion of third separator 432 is operable for containing HF and volatility reducing additive. Conduit 430 is operably related in fluid flow communication with conduit 434. Conduit 434 provides thirteenth conduit means for withdrawing a purge stream from conduit 430.

Third separator 432 is operably related in fluid flow communication via conduit 436 to settler 408. Conduit 436 provides fourteenth conduit means for withdrawing a third separator bottoms stream from the lower portion of third separator 432 and for introducing at least a portion of the third separator bottoms stream into the intermediate portion of settler 408. Third separator 432 is also operably related in fluid flow communication with conduit 438 which provides fifteenth conduit means for removing ASO from the upper portion of third separator 432.

In addition, the inventive system or apparatus 40 can include a control system operably related to conduits 418, 421, 424, 426, 430, and 434 which provides control means for varying the flow rates within said conduits for controlling the water concentration in the catalyst mixture phase to a level equal to a set-point water weight percent, based on the total weight of the catalyst mixture phase. The set-point water weight percent is preferably in the range of from about 0.5 to about 3.0, and more preferably from 1.0 to 2.0.

Dash lines, which designate signal lines in the drawings, are electrical or pneumatic in this preferred embodiment. However, the invention is also applicable to mechanical, hydraulic, or other signal means for transmitting information. In almost all control systems some combination of these types of signals will be used. However, the use of any other type of signal transmission, compatible with the process and equipment in use, is within the scope of the invention.

A digital computer is used in the preferred embodiment of this invention to calculate the required control signal based on measured process parameters as well as set points supplied to the computer. Any computer control system having software that allows operation in a real time environment for reading values of external variables and transmitting signals is suitable for use in this invention.

Signal lines are also utilized to represent the results of calculations carried out in a digital computer and the term "signal" is utilized to refer to such results. Thus, the term signal is used not only to refer to electrical currents or pneumatic pressures but is also used to refer to binary representations of a calculated or measured value.

The controllers shown may utilize the various modes of control such as proportional, proportional-integral, proportional-derivative, or proportional-integral-derivative. In this preferred embodiment, proportional-integral-derivative controllers are utilized but any controller capable of accepting two input signals and producing a scaled output signal, representative of a comparison of the two input signals, is within the scope of the invention.

The scaling of an output signal by a controller is well known in control system art. Essentially, the output of a controller may be scaled to represent any desired factor or variable. An example of this is where a desired flow rate and an actual flow rate are compared by a controller. The output could be a signal representative of a desired change in the flow rate of some liquid necessary to make the desired and actual flows equal. On the other hand, the same output signal could be scaled to represent a percentage or could be scaled to represent a temperature change required to make the desired and actual flows equal. If the controller output can range from 0 to 10 volts, which is typical, then the output signal could be scaled so that an output signal having a voltage level of 5.0 volts corresponds to 50 percent of some specified flow rate.

The various transducing means used to measure parameters which characterize the process and the various signals generated thereby may take a variety of forms or formats. For example, the control elements of the system can be implemented using electrical analog, digital electronic, pneumatic, hydraulic, mechanical or other similar types of equipment or combinations of one or more such equipment types. While the presently preferred embodiment of the invention preferably utilizes a combination of pneumatic final control elements in conjunction with electrical analog signal handling and translation apparatus, the apparatus and method of the invention can be implemented using a variety of specific equipment available to and understood by those skilled in the process control art.

Likewise, the format of the various signals can be modified substantially in order to accommodate signal format requirements of the particular installation, safety factors, the physical characteristics of the measuring or control instruments and other similar factors. For example, a raw flow measurement signal produced by a differential pressure orifice flow meter would ordinarily exhibit a generally proportional relationship to the square of the actual flow rate. Other measuring instruments might produce a signal which is proportional to the measured parameter, and still other transducing means may produce a signal which bears a more complicated, but known, relationship to the measured parameter.

Regardless of the signal format or the exact relationship of the signal to the parameter which it represents, each signal representative of a measured process parameter or representative of a desired process value will bear a relationship to the measured parameter or desired value which permits designation of a specific measured or desired value by a specific signal value. A signal which is representative of a process measurement or desired process value is therefore one from which the information regarding the measured or desired value can be readily retrieved regardless of the exact mathematical relationship between the signal units and the measured or desired process units.

Referring again to FIG. 4, the control system can be described as follows.

Conduit 418 is operably related to a first control valve 440 interposed therein which provides first control valve means for adjusting the flow rate of the HF/water stream through conduit 418. Conduit 421 is operably related to a second control valve 441 interposed therein which provides second control valve means for adjusting the flow rate of the portion of the HF/water stream through conduit 421. Conduit 426 is operably related to a third control valve 442 interposed therein which provides third control valve means for adjusting the flow rate of the catalyst mixture phase regeneration stream through conduit 426. Conduit 430 is operably related to a fourth control valve 444 interposed therein which provides fourth control valve means for adjusting the flow rate of the second separator bottoms stream through conduit 430. Conduit 434 is operably related to a fifth control valve 446 interposed therein which provides fifth control valve means for adjusting the flow rate of the purge stream through conduit 434.

Operably associated with each of the conduits 418, 421, 426, 430 and 434 is a respective flow transducer 448, 449, 450, 452 and 454, each of which produces a respective flow signal 456, 457, 458, 460 and 462 which is representative of the volume flow rate of the material carried through the conduit with which it is associated. Flow transducers 448, 449, 450, 452 and 454 can comprise flow measuring devices, such as orifice plates, located within conduits 418, 421, 426, 430 and 434, respectively, for measuring the volume flow rates.

Analyzer 464, which is preferably a near infrared analyzer, such as that described in U.S. Pat. No. 6,096,553, provides means for establishing a signal 466 representative of the actual value of the water concentration of the catalyst mixture phase. Analyzer 464 is preferably operably related to conduit 424 and is adapted to deliver, in response to the analysis of the catalyst mixture phase, signal 466. Analyzer 464 can include off-line analysis of the sample of the catalyst mixture phase.

A computer calculation block 468, providing computer means and preferably associated with a distributed control system, receives as inputs thereto the flow rate signals, 456, 457, 458, 460 and 462, water concentration signal 466, and an operator entered signal 470 which is representative of the desired value for the set-point water weight percent of the catalyst mixture phase flowing in conduit 424. Computer calculation block 468 establishes output signals 472, 473, 474, 476 and 478, each responsive to signals 456, 457, 458, 460 and 462 and to the difference between signals 466 and 470. Signals 472, 473, 474, 476, and 478 are scaled to be representative of the flow rates of: the HF/water stream in conduit 418, the portion of the HF/water stream, the catalyst mixture phase regeneration stream in conduit 426, the second separator bottoms stream in conduit 430, and the purge stream in conduit 434, respectively, required to maintain the actual value of the water concentration of the catalyst mixture phase represented by signal 466 substantially equal to the desired value of the set-point water weight percent of the catalyst mixture phase represented by signal 470.

Signal 472 is provided as a set-point input to flow controller 480. Also provided as a processing variable input to flow controller 480 is flow rate signal 456 which is representative of the actual flow rate of the HF/water stream in conduit 418. Flow controller 480 provides an output signal 482 which is responsive to the difference between signals 472 and 456. Signal 482 is scaled to be representative of the position of control valve 440 required to maintain the flow rate represented by signal 456 substantially equal to the flow rate represented by signal 472.

Signal 473 is provided as a set-point input to flow controller 481. Also provided as a processing variable input to flow controller 481 is flow rate signal 457 which is representative of the actual flow rate of the portion of the HF/water stream in conduit 421. Flow controller 481 provides an output signal 483 which is responsive to the difference between signals 473 and 457. Signal 483 is scaled to be representative of the position of control valve 441 required to maintain the flow rate represented by signal 457 substantially equal to the flow rate represented by signal 473.

Signal 474 is provided as a set-point input to flow controller 484. Also provided as a processing variable input to flow controller 484 is flow rate signal 458 which is representative of the actual flow rate of the catalyst mixture phase regeneration stream in conduit 426. Flow controller 484 provides an output signal 486 which is responsive to the difference between signals 474 and 458. Signal 486 is scaled to be representative of the position of control valve 442 required to maintain the flow rate represented by signal 458 substantially equal to the flow rate represented by signal 474.

Signal 476 is provided as a set-point input to flow controller 488. Also provided as a processing variable input to flow controller 488 is flow rate signal 460 which is representative of the actual flow rate of the second separator bottoms stream in conduit 430. Flow controller 488 provides an output signal 490 which is responsive to the difference between signals 476 and 460. Signal 490 is scaled to be representative of the position of control valve 444 required to maintain the flow rate represented by signal 460 substantially equal to the flow rate represented by signal 476.

Signal 478 is provided as a set-point input to flow controller 492. Also provided as a processing variable input to flow controller 492 is flow rate signal 462 which is representative of the actual flow rate of the purge stream in conduit 434. Flow controller 492 provides an output signal 494 which is responsive to the difference between signals 478 and 462. Signal 494 is scaled to be representative of the position of control valve 446 required to maintain the flow rate represented by signal 462 substantially equal to the flow rate represented by signal 478.

CALCULATED EXAMPLE

This example illustrates water removal from an alkylation process system using the inventive process.

Alkylation Process Conditions Assumptions:

2,000 barrels (bbl) of alkylate produced per day 21,500 bbl settler effluent/day flowing to first fractionator (where alkylate is taken as bottoms stream) having a density of 201.6 lbs/bbl.

HF acid complex solubility in hydrocarbon settler effluent=1% by weight 0.5–1 wt. % of the soluble HF acid complex is water (resulting in 50–100 ppm water in settler effluent)

100% of the soluble HF acid complex in the settler effluent passes overhead from the first fractionator and is at least partially condensed.

82% of the condensed acid components are recovered as boot acid from the overhead accumulator.

Calculations:

(21,500 bbl settler effluent/day)*(201.6 lbs./bbl)*(1 day/24 hours)=180,392 lbs settler effluent/hour At 0.5 wt. % water in the soluble HF acid complex and 1 wt. % soluble HF acid complex in the settler effluent, the water and HF mass flows are:

0.5 wt. % water*1 wt. % soluble HF acid complex*180,392 lbs settler effluent/hour=9 lbs. of water/hour and;

1 wt. % soluble HF acid complex*180,392 lbs. settler effluent/hour=1,804 lbs. of HF/hour.

Total HF acid and water=1,813 lbs/hour.

If the HF acid and water above, once condensed, are saturated with 6 wt. % hydrocarbon, the condensed acid would be ~93.5 wt. % HF, 0.47 wt. % water, and 6 wt. % hydrocarbon.

82% recovery of the above condensed acid components in the form of boot acid results in 1,487 lbs./hour of acid components.

This boot acid stream is routed to a second fractionator (typically called a rerun column). At the above stated 82% recovery, the amount of water passed to the second fractionator is about 7 lbs./hour.

Running the second fractionator to reject $HF/H_2O$ azeotrope from the bottom of the column would yield 3.5 lbs/hour of water rejection at 50% rejection efficiency (which is typical). At 75% rejection rate (which is achievable), the amount of water rejection would be 5.3 lbs/hour.

For this size of unit, the water removal rate is typically 7–10 lbs water/day. Thus, either 3.5 or 5.3 lbs of water/hour would compare very favorably with the typical design water removal by removing the daily required amount of water in 2 to 3 hours. In addition, the percentage of acid components recovered from the overhead accumulator as boot acid can easily be greater than 82%, which would further increase the water removal rate.

Running the alkylation system using the inventive method for 24 hours would reject 84 lbs. of water/day at 3.5 lbs of water removed/hour and 127 lbs of water/day at 5.5 lbs of water removed/hour. At 70,000 lbs acid inventory (which is typical), this would reduce the wt. % water in the acid by about 0.1 to about 0.2 percentage points per day.

Whereas this invention has been described in terms of the preferred embodiments, reasonable variations and modifications are possible by those skilled in the art. Such modifications are within the scope of the described invention and appended claims.

That which is claimed is:

1. A system comprising:

an alkylation reactor;

a settler, having an upper portion, an intermediate portion and a lower portion;

a first separator, having an upper portion, an intermediate portion and a lower portion;

a second separator, having an upper portion, an intermediate portion and a lower portion;

a third separator, having an upper portion, an intermediate portion and a lower portion;

a condenser unit;

first conduit means operably related to said alkylation reactor for introducing a hydrocarbon feedstock comprising olefins and isoparaffins into said alkylation reactor;

second conduit means operably related to said alkylation reactor for introducing a catalyst mixture comprising a volatility reducing additive, hydrofluoric acid and water into said alkylation reactor;

third conduit means operably related to said alkylation reactor and operably related to said settler for withdrawing a reaction zone effluent from said alkylation reactor and for introducing said reaction zone effluent into said intermediate portion of said settler, said upper portion of said settler being operable for containing a hydrocarbon phase separated from said reaction zone effluent and said lower portion of said settler being operable for containing a catalyst mixture phase separated from said reaction zone effluent;

fourth conduit means operably related to said settler and operably related to said first separator for withdrawing at least a portion of said hydrocarbon phase from said upper portion of said settler and for introducing said at least a portion of said hydrocarbon phase into the intermediate portion of said first separator;

fifth conduit means operably related to said first separator and operably related to said condenser unit for withdrawing an overhead stream from said upper portion of said first separator and for introducing said overhead stream into said condenser unit;

sixth conduit means operably related to said condenser unit and operably related to said second separator for withdrawing an HF/water stream from said condenser unit and for introducing said HF/water stream into said intermediate portion of said second separator;

seventh conduit means operably related to said sixth conduit means and operably related to said settler for withdrawing a portion of said HF/water stream from said sixth conduit means and for introducing said portion of said HF/water stream into said intermediate portion of said settler;

eighth conduit means operably related to said first separator for withdrawing an alkylate product stream from said first separator;

ninth conduit means operably related to said settler and operably related to said alkylation reactor for withdrawing at least a portion of said catalyst mixture phase from said settler and for introducing said at least a portion of said catalyst mixture phase into said alkylation reactor;

tenth conduit means operably related to said settler and operably related to said second separator for withdrawing a catalyst mixture phase regeneration stream from the lower portion of said settler and for introducing said catalyst mixture phase regeneration stream into the intermediate portion of said second separator;

eleventh conduit means operably related to said second separator and operably related to said settler for withdrawing a second separator overhead stream from the upper portion of said second separator and for introducing said second separator overhead stream to the intermediate portion of said settler;

twelfth conduit means operably related to said second separator and operably related to said third separator for withdrawing a second separator bottoms stream from the lower portion of said second separator and for introducing said second separator bottoms stream to the intermediate portion of said third separator, said upper portion of said third separator being operable for containing ASO and said lower portion of said third separator being operable for containing HF and volatility reducing additive;

thirteenth conduit means operably related to said twelfth conduit means for withdrawing a purge stream from said twelfth conduit means; and fourteenth conduit means operably related to said third separator and operably related to said settler for withdrawing a third separator bottoms stream from said lower portion of said third separator and for introducing at least a portion of said third separator bottoms stream into said intermediate portion of said settler.

2. A system as recited in claim 1 further comprising control means operably related to said sixth conduit means, said seventh conduit means, said ninth conduit means, said tenth conduit means, said twelfth conduit means, and said thirteenth conduit means for controlling the water concentration in said catalyst mixture phase regeneration stream to a level equal to a set point water wt. %, based on the total weight of said catalyst mixture phase.

3. A system as recited in claim 2 wherein said control means comprises:

means for establishing a first signal, operably related to said sixth conduit means, representative of the actual flow rate of said HF/water stream;

means for establishing a second signal, operably related to said seventh conduit means, representative of the actual flow rate of said portion of said HF/water stream;

means for establishing a third signal, operably related to said ninth conduit means, representative of the actual value of said water concentration of said catalyst mixture phase;

means for establishing a fourth signal, operably related to said tenth conduit means, representative of the actual flow rate of said catalyst mixture phase regeneration stream;

means for establishing a fifth signal representative of said set point water wt. % of said catalyst mixture phase;

means for establishing a sixth signal, operably related to said twelfth conduit means, representative of the actual flow rate of said second separator bottoms stream;

means for establishing a seventh signal, operably related to said thirteenth conduit means, representative of the actual flow rate of said purge stream;

computer means for comparing said third signal to said fifth signal and establishing an eighth signal, a ninth signal, a tenth signal, an eleventh signal and a twelfth signal, each responsive to said first signal, said second signal, said fourth signal, said sixth signal, said seventh signal and to the difference between said third signal and said fifth signal, wherein said eighth signal, said ninth signal, said tenth signal, said eleventh signal and said twelfth signal are scaled to be representative of the flow rates of: said HF/water stream, said portion of said HF/water stream, said catalyst mixture phase regeneration stream, said second separator bottoms stream and said purge stream, respectively, required to maintain the actual value of said water concentration represented by said third signal equal to said set point water wt. % represented by said fifth signal;

means for comparing said first signal and said eighth signal and for establishing a thirteenth signal which is responsive to the difference between said first signal and said eighth signal;

first control valve means operably located in said sixth conduit means for adjusting the flow rate of said HF/water stream in response to said thirteenth signal;

means for comparing said second signal and said ninth signal and for establishing a fourteenth signal which is responsive to the difference between said second signal and said ninth signal;

second control valve means operably located in said seventh conduit means for adjusting the flow rate of said portion of said HF/water stream in response to said fourteenth signal;

means for comparing said fourth signal and said tenth signal and for establishing a fifteenth signal which is responsive to the difference between said fourth signal and said tenth signal;

third control valve means operably located in said tenth conduit means for adjusting the flow rate of said catalyst mixture phase regeneration stream in response to said fifteenth signal;

means for comparing said sixth signal and said eleventh signal and for establishing a sixteenth signal which is responsive to the difference between said sixth signal and said eleventh signal;

fourth control valve means operably located in said twelfth conduit means for adjusting the flow rate of said second separator bottoms stream in response to said sixteenth signal;

means for comparing said seventh signal and said twelfth signal and for establishing a seventeenth signal which is responsive to the difference between said seventh signal and said twelfth signal;

fifth control valve means operably located in said thirteenth conduit means for adjusting the flow rate of said purge stream in response to said seventeenth signal.

4. A system as recited in claim 3 wherein said means for establishing said third signal comprises a near infrared analyzer means for determining the actual water concentration of said catalyst mixture phase, and for establishing said third signal.

5. A system as recited in claim 1 further comprising fifteenth conduit means operably related to said third separator for withdrawing ASO from said upper portion of said third separator.

* * * * *